United States Patent
Emborg et al.

(10) Patent No.: US 6,811,372 B1
(45) Date of Patent: Nov. 2, 2004

(54) DEVICE AT AN ACOUSTIC LINER

(75) Inventors: Urban Emborg, Ljungsbro (SE); Sohan Sarin, Linkoping (SE)

(73) Assignee: A2 Acoustics AB, Linkoping (SE)

( * ) Notice: Subject to any disclaimer, the term of this patent is extended or adjusted under 35 U.S.C. 154(b) by 0 days.

(21) Appl. No.: 10/149,112

(22) PCT Filed: Nov. 22, 2000

(86) PCT No.: PCT/SE00/02291

§ 371 (c)(1), (2), (4) Date: Oct. 15, 2002

(87) PCT Pub. No.: WO01/43119

PCT Pub. Date: Jun. 14, 2001

(30) Foreign Application Priority Data

Dec. 7, 1999 (SE) .............................................. 9904445

(51) Int. Cl.[7] .............................................. F03B 11/04
(52) U.S. Cl. ...................... 415/119; 415/196; 181/292; 181/293
(58) Field of Search ................................ 415/118, 119, 415/196, 9; 181/290, 291, 292, 293, 294

(56) References Cited

U.S. PATENT DOCUMENTS 3,890,060 A * 6/1975 Lipstein ...................... 415/119
4,410,065 A   10/1983 Harvey
5,702,230 A * 12/1997 Kraft et al. .................. 415/119

FOREIGN PATENT DOCUMENTS

EP   0702141   3/1996
GB   1321073   6/1973

* cited by examiner

*Primary Examiner*—Edward K. Look
*Assistant Examiner*—Dwayne White
(74) *Attorney, Agent, or Firm*—Swidler Berlin Shereff Friedman, LLP

(57) ABSTRACT

A device at an acoustic liner for an apparatus generating sound comprises means (12) adapted to enable changes of the value of the acoustic impedance of the liner.

23 Claims, 3 Drawing Sheets

DEVICE AT AN ACOUSTIC LINER

FIELD OF THE INVENTION AND PRIOR ART

The present invention relates to a device at an acoustic liner for an apparatus generating sound. "Apparatus generating sound" comprises all apparatuses in which sound is generated upon operation thereof, in which the sounds usually are not desired. Different types of engines, such as diesel engines and gas turbine apparatuses may be mentioned as examples. The invention is particularly, but not exclusively directed to the latters, which is the reason for treating them hereafter.

"Gas turbine apparatus" is here to be given a broad sense and comprises all types of apparatuses having a turbine or propeller wheel generating an air flow of gas from an inlet to an outlet of the turbine, such as for example an industrial gas turbine or an aeroplane engine of the jet type.

Important sounds not desired are usually generated in such a gas turbine apparatus, and one or several of said acoustic liners are for this reason arranged in the gas turbine apparatus, preferably along the walls delimiting the gas flow therethrough.

The case of silencing of noise in a gas turbine apparatus in the form of an aeroplane engine with a said acoustic liner will hereinafter be described for illuminating the invention and the problem to be solved thereby, but not for acting restricingly in any way. Such an aeroplane engine 1 is in a simplified cross section shown in FIG. 1. The engine has a inner tube 2 with an inlet 3 and an outlet 4. The air is drawn into the inlet 3 through rotation of the turbine wheel 5 and is accelerated rearwardly, where atomized fuel is supplied to the air and combustion thereof takes place in a combustion space 6, so that the gases reaching the outlet 4 will have a very high temperature, usually 500–600° C. An engine of this type may cause considerable noise, and there are a number of reasons for attempting to limit this noise as far as possible. Such a reason is that the noise seriously disturbs the environment of the aeroplane, especially at start and landing. Another reason, which is a result of the one first mentioned, is that most airports have started to put higher demands on low noise levels of aeroplanes, and in many places the aviation companies have to pay landing fees increasing strongly with an increased noise level of the aeroplane in question. It is also conceivable that aeroplanes, the engines of which cause noise above a certain level, will not even get permission to land on certain airports.

Acoustic liners, i.e. structures silencing noise, are for this sake arranged inside the engine, as indicated in FIG. 1. These acoustic liners have usually a cavity structure 7 of honeycomb type with a cover layer 8 arranged thereon and being at least partially gas permeable. The cavities are dimensioned, especially with respect to depth, so as to absorb sound within the frequency range including the most serious sounds, which in this case usually is 200–500 Hz for exhaust sound and 2000–5000 Hz for inlet sound. If the perforations allowing the gas permeability of the layer 8 are made very small, more exactly with a diameter smaller than 10 microns, the liner will be linear, which means that the acoustic impedance thereof will not be changed with the magnitude of gas flow and the air pressure layer at the liner. It is usually desired that the liner is linear, since substantially the same acoustic impedance may be ensured for different operation conditions, as will be the case for instance start with respect to cruise and/or landing. A cover layer of a wire fabric densely woven is for this reason usually arranged in the liner 9 in the inlet 3 of the engine, but at the outlet 4 where the temperature is considerably higher, it is not possible to arrange such a fabric, but a perforated sheet 10 is instead arranged on the liner 11. The perforations of this sheet are to large for making this liner linear, so that it will instead be non-linear, which means that the acoustic impedance thereof is changed with the magnitude of the gas flow and the sound pressure level, which means that such a liner will function in a satisfying way only within a very narrow range of operation conditions. This makes it necessary to compromise, so that the noise silencing function of the liner 11 for the frequencies in question will for example be comparatively good during a certain part of the start phase of the aeroplane, while it perhaps will be considerably more worse during other parts of the start phase and at cruise and/or landing.

SUMMARY OF THE INVENTION

The object of the present invention is to provide a device of the type defined in the introduction, which makes it possible to take care of the noise problems at apparatuses generating sound of the type described above in a better way than before.

This object is according to the invention obtained by providing such a device with means adapted to enable changes of the value of the acoustic impedance of the liner. By providing such means, which means that an adaption of the acoustic impedance of the liner to the operation conditions prevailing may be made, it will be possible to obtain a good silencing property of the liner over a wider operation range than have been possible before. It is particularly advantageous that the liner is a non-linear acoustic liner, since the disadvantages with respect to the sensitivity of the acoustic impedance for the flow and air pressure of such a liner may be converted into advantages, since it will be possible to regulate the acoustic impedance of the liner through said means so that this is advantageous in most different operation situations. Thus, the acoustic impedance of the liner may through said means be brought to an optimum value while considering the different disturbing frequencies and the different needs for silencing prevailing during different operation conditions, such as in the case of an aeroplane engine, at start, cruise and landing.

According to a preferred embodiment of the invention said means are adapted to enable an adjustment of the value of the acoustic impedance of the liner in dependence on the operation conditions of the apparatus, in which this is preferably made automatically, by sending values of different parameters with respect to operation conditions detected to a control unit adapted to control said means. Thus, said means are preferably adapted to enable a modification of the acoustic impedance of the liner during operation of the apparatus.

In the case of a gas turbine apparatus in the form of an aeroplane engine said means are advantageously adapted to co-operate with members for measuring the altitude of the aeroplane so as to adjust the acoustic impedance of the liner in dependence on the altitude prevailing, and/or said means may be arranged to co-operate with members for measuring the number of revolutions of the aeroplane engine so as to adjust the acoustic impedance of the liner in dependence on the current number of revolutions. These are some parameters which may give a hint of what acoustic impedance the liner should have at existing operation conditions. Another such parameter could be the time differential quotient of the altitude of the aeroplane, i.e. the climbing speed or the rate of descent.

According to another preferred embodiment of the invention said means comprise members adapted to change the acoustic impedance of the liner by changing the temperature of the gas at the liner. By such a temperature change also the velocity of air in the gas in question and by that the acoustic impedance of the liner is changed, so that this will be the one desired at the operation conditions in question.

According to a very preferred embodiment of the invention said means comprises members adapted to conduct a film of gas along and past the acoustic liner for adjusting the acoustic impedance of the liner. By conducting a film of gas along the liner it could be possible to adjust both the temperature of the gas at the liner and the flow velocity thereof, which in a non-linear filter would mean an adjustment of the acoustic impedance of the filter. It is then particularly advantageous if said members are adapted to conduct a film of gas along and past the acoustic liner for cooling thereof. A utilisation of this film cooling technique in connection with an acoustic liner is something totally new, and by varying the flow velocity and/or the temperature of the gas film the acoustic impedance of the liner may be varied.

It is also possible to arrange members adapted to heat the gas at the acoustic liner for changing the acoustic impedance of the acoustic liner by changing the gas temperature at the liner. The cooling film members may then very well be combined with the heating members and these may be operated during different phases of the operation of the apparatus, in the case of an aeroplane engine during the different flight phases.

According to another preferred embodiment of the invention, which is adapted to acoustic liners having a cavity structure of honeycomb type with a cover layer arranged thereon and being at least partially gas permeable, said means comprise members adapted to change the resistance to flow of gas through the cover layer to and from the cavities. This may for example be obtained by a change of the size of through-holes arranged in said cover layer, and it results in a change of the acoustic impedance of the liner.

According to another preferred embodiment of the invention said means comprise members adapted to change the flow resistance for gases of the gas turbine apparatus flowing past the acoustic liner. Also such a change of the flow resistance results in a changed acoustic impedance of the liner. According to another very preferred embodiment of the invention said means are adapted to enable an independent local influence upon the acoustic impedance of the liner for enabling variation of the acoustic impedance of the liner over the extension thereof in the gas flow direction of the gas turbine apparatus. The acoustic impedance of the liner could through this be varied according to desires in said gas flow direction for adaption thereof to possibly different frequencies of the most disturbing sounds in different parts of the gas turbine apparatus.

According to another preferred embodiment of the invention the acoustic liner is arranged in the outlet part of the gas turbine apparatus behind the combustion of fuel as seen in the flow direction. In this part of the gas turbine apparatus, where the temperature may be very high, non-linear liner having a good function within a very restricted operation range could so far be arranged, so that it is especially advantageous to enable an adaption of the acoustic impedance of the liner there. Furthermore, in the case of use of the film cooling technique less costly material may be used for the liner exactly there and by that costs be saved.

By utilising the film cooling technique it is also possible, if desired, to even allow an arrangement of a linear liner of conventional type in some cases, i.e. provided with a cover layer of wire fabric, in the outlet of the gas turbine apparatus. The acoustic liner could then be at least partially made of a composite material, and said members are adapted to cool the liner to such a low temperature that the composite material used may resist it. This means then both a saving of costs in the form of a less expensive material for the liner and a possibility to make the entire aeroplane engine lighter.

The invention also relates to methods for silencing of noise in an apparatus generating sound having an acoustic liner according to the appended method claims. Advantages of these methods appear clearly from the discussion above of the different preferred embodiments of the devices according to the invention.

Further advantages as well as advantageous features of the invention appear from the following description and the other dependent claims.

BRIEF DESCRIPTION OF THE DRAWINGS

With reference to the appended drawings, below follows a description of preferred embodiments of the invention cited as examples.

In the drawings.

DETAILED DESCRIPTION OF PREFERRED EMBODIMENTS OF THE INVENTION

Figure 1:
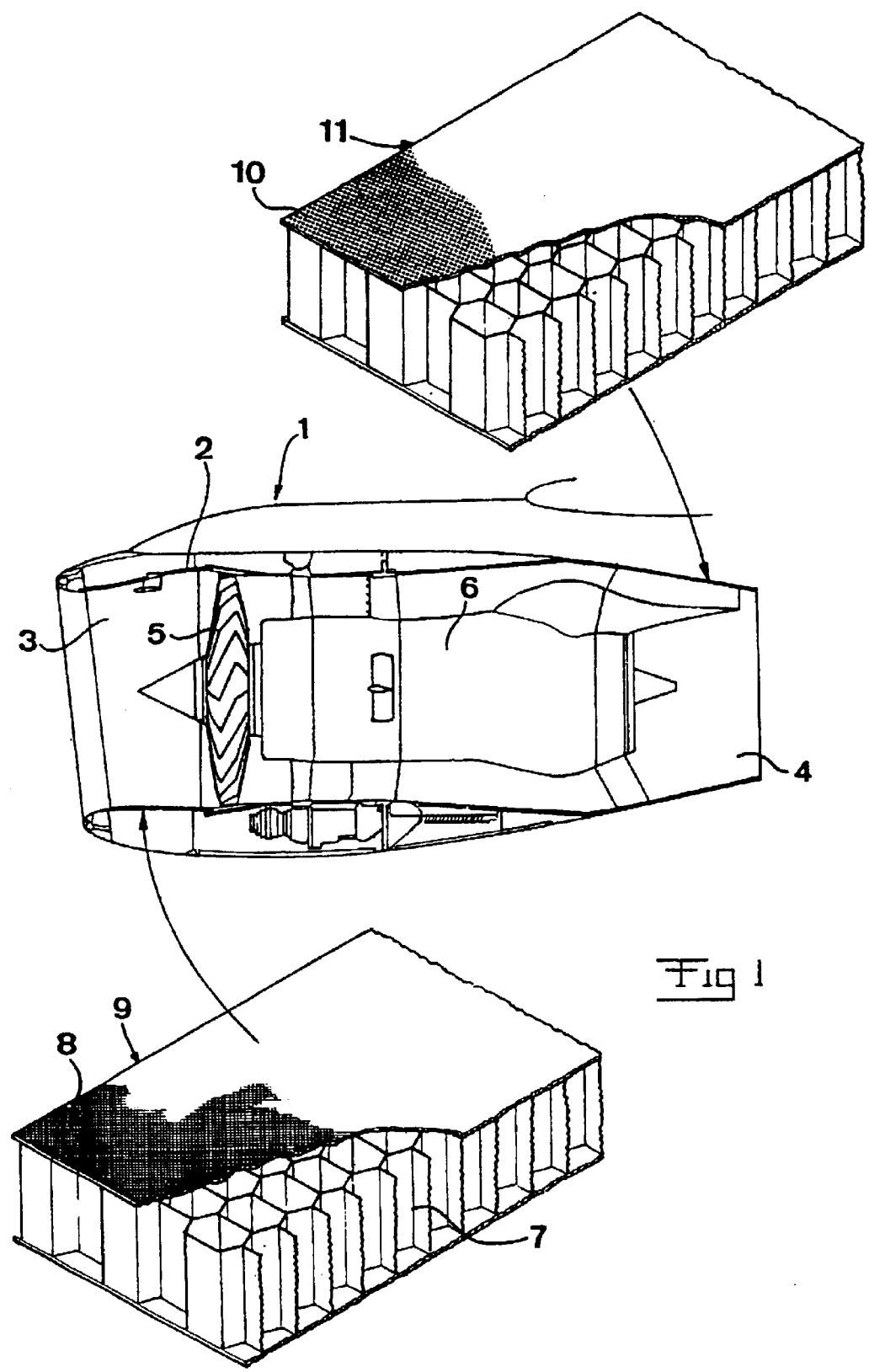
FIG. 1 is a schematic section view through an aeroplane engine illustrating how it is conventionally provided with acoustic liners.
Figure 2:
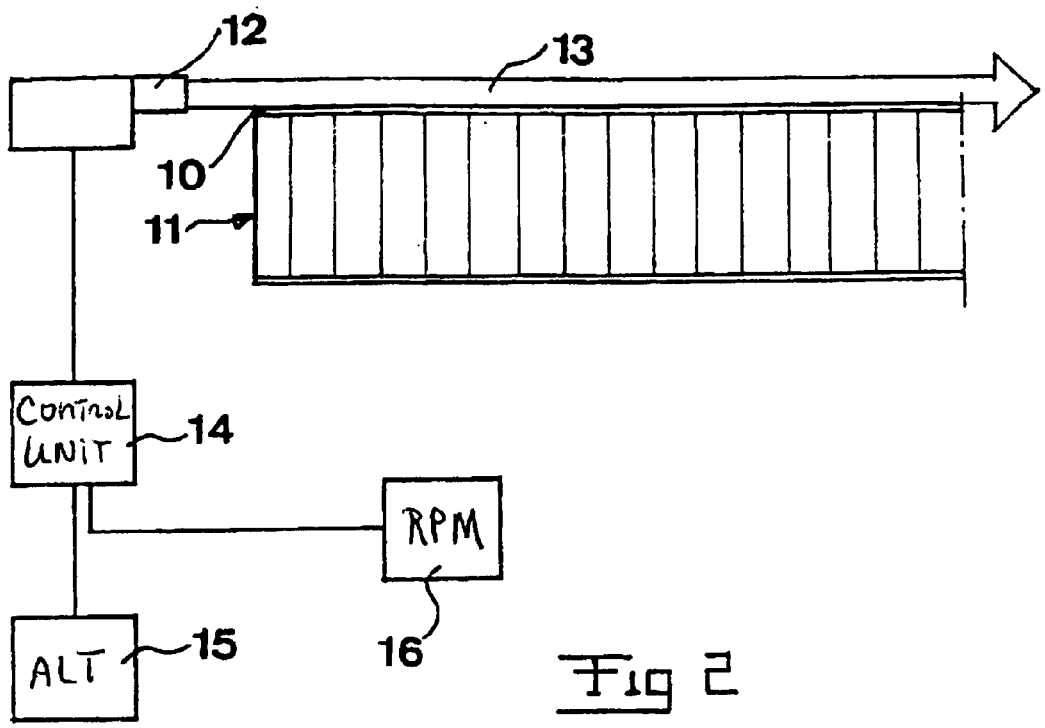
FIG. 2 is a simplified detail view of an acoustic liner and equipment connected thereto of a device according to a preferred embodiment of the invention.

The acoustic impedance of an acoustic liner is for a non-linear liner depending upon the temperature of the gas at the liner and the flow velocity of the gas at the liner. The acoustic impedance is also depending on the depth of the cavities forming the cavity structure 7. In the device according to FIG. 2 members 12 are adapted to generate and conduct a film 13 of cold air past the acoustic liner for adjusting the acoustic impedance thereof. The temperature and the flow velocity of this thin film of cold air may be changed for adjusting the acoustic impedance of the liner, and it is even possible to entirely shut off said members 12 would that be desired during certain operation conditions. The device has a control unit 14 for controlling the function of the member 12 depending on the current operation conditions, which may in the case of an aeroplane engine be for example the altitude of the aircraft and/or the number of revolutions of the turbine wheel of the engine, which is indicated by the members 15, 16. The member 12 may be circumferentially arranged inside the tube 2 for generating a circumferential air film sweeping over the liner.

Figure 3:
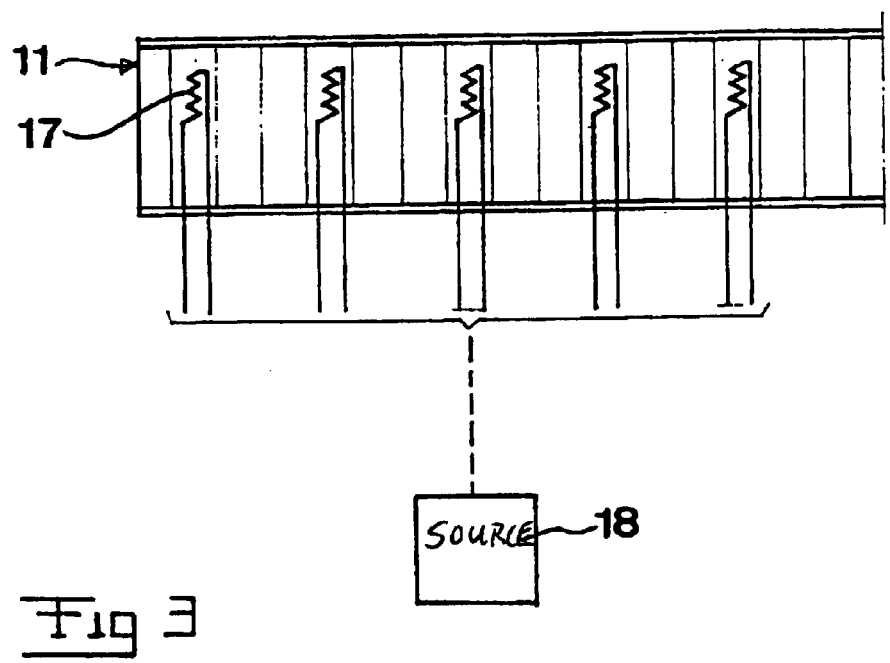
FIG. 3 is a view corresponding to FIG. 2 of a device according to a second preferred embodiment of the invention.

A device according to a second preferred embodiment of the invention is schematically illustrated in FIG. 3, in which members 17 for heating the gases flowing past the liner are adapted to receive energy from a source 18. The heating members 17 are preferably individually controlled for changing the acoustic impedance in the extension of the liner in parallel with the gas flow through the gas turbine apparatus. The heating members 17 may advantageously be combined with the members 12 for providing a film of cold air for enabling a variation of the acoustic impedance of the liner over a wider spectrum.

Figure 4:
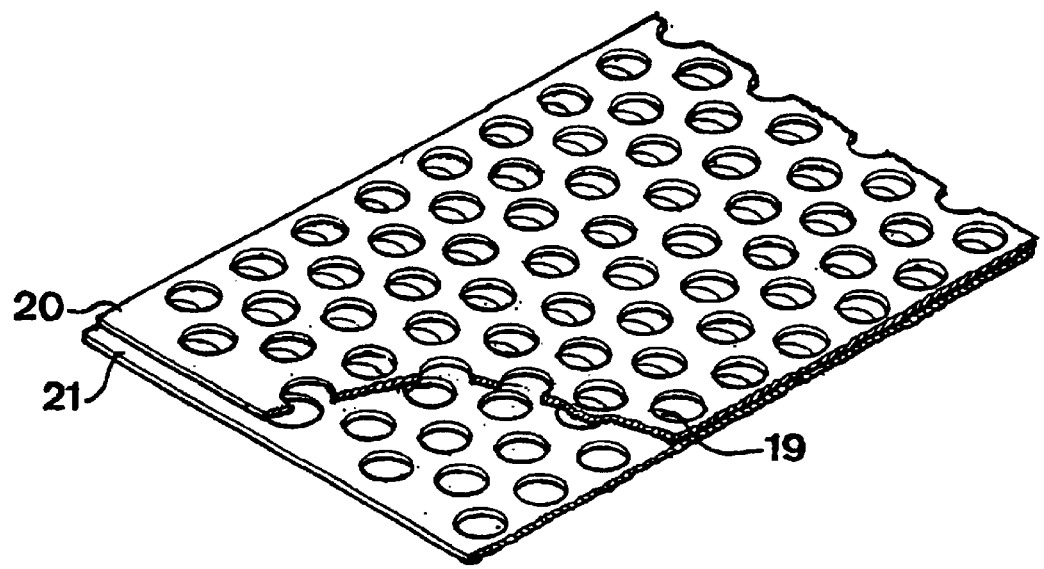
FIG. 4 is a view corresponding to FIG. 2 of a device according to a third preferred embodiment of the invention.

It is illustrated in FIG. 4 how it is possible to vary the acoustic impedance of the liner in question by varying the size of the holes of the cover layer for communication between cavities and the very turbine tube. This has here been achieved by changing two thin layers 20, 21, for example sheets, provided with bores, on top of each other and displacing the layers with respect to each other for adjusting the size of the openings 19 through the two layers. There is of course other ways to vary the size and shape of the cavities.

Figure 5:
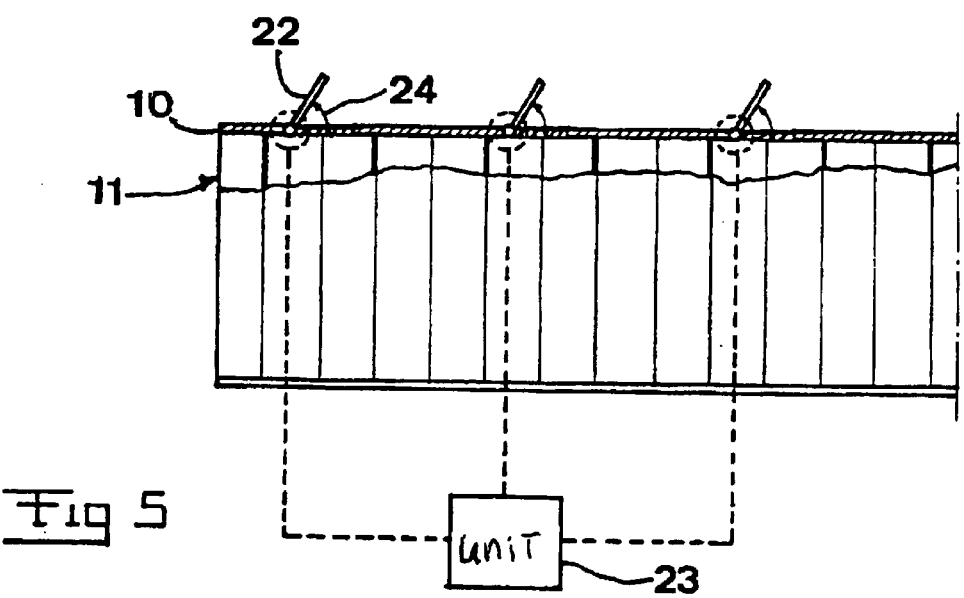
FIG. 5 is a view corresponding to FIG. 2 of a device according to a fourth preferred embodiment of the invention.

Finally, FIG. 5 illustrates an arrangement of a number of obstacles 22 for the flow of gases past the liner, so that the flow resistance and by that the acoustic impedance of the liner will be changed. The device has a unit 23 for controlling the obstacles 22 by folding these down to different extents, such as illustrated through the arrows 24.

It will through a device according to the invention be possible to adapt the acoustic impedance of an acoustic liner in an aeroplane engine for obtaining a value being an optimum at different operation conditions, so that noise having exactly the frequencies being not desired in a given operation condition may be reduced considerably and the need of silencing existing under exactly this operation condition may be met in the best possible way and an optimum silencing of noise may be obtained during different flight phases.

The embodiment of cooling of the gas at the liner and by that the liner is especially interesting at industrial gas turbines, where an adaption of the acoustic impedance of the liner is not necessarily most important, but it would be most important to be able to use a cheaper, less heat resistant material for making the liner.

The invention is of course not in any way restricted to the preferred embodiments described above, but many possibilities to modifications thereof would be apparent to a man with ordinary skill in the art without departing from the basic idea of the invention.

It would for example be possible to combine the embodiments shown above in an arbitrary way.

Each embodiment may also without difficulties be modified. For example instead of two cover layers displaceable with respect to each other to a small extent two or more cover layers provided with holes and having different hole sizes may be provided and one single such cover layer at the time may be pushed in over the cavity structure for combining this with holes of exactly the size being the most suitable for the operation conditions prevailing.

What is claimed is:

1. A device at an acoustic liner for an apparatus generating sound, comprising:
   means adapted to enable changes of the value of the acoustic impedance of the liner by changing the temperature of the gases at the liner.

2. A device according to claim 1, wherein the liner is a non-linear acoustic liner.

3. A device according to claim 1, wherein said means are adapted to effect an adjustment of the value of the acoustic impedance of the liner in accordance with the operation conditions of the apparatus.

4. A device according to claim 3, wherein said apparatus is an aeroplane engine, and said means are adapted to cooperate with members for measuring the altitude of the aeroplane for adjusting the acoustic impedance of the liner in accordance with the current altitude.

5. A device according to claim 3, wherein said means are adapted to cooperate with members for measuring the number of revolutions of the aeroplane engine for adjusting the acoustic impedance of the liner in accordance with the current number of revolutions.

6. A device according to claim 1, wherein said means are adapted to enable a modification of the acoustic impedance of the liner during operation of the apparatus.

7. A device according to claim 1, wherein the acoustic liner is arranged in an apparatus in the form of a gas turbine apparatus.

8. A device according to claim 7, the acoustic liner is arranged in a gas turbine apparatus in the form of an aeroplane engine.

9. A device according to claim 7, wherein said means comprise members adapted to change the flow resistance for gases in the gas turbine apparatus flowing past the acoustic liner.

10. A device according claim 7, wherein said means are adapted to enable an independent local influence upon the acoustic impedance of the liner for enabling varying of the acoustic impedance of the liner over the extension thereof in the gas flow direction of the gas turbine apparatus.

11. A device according to claim 7, wherein the acoustic liner is arranged in the outlet part of the gas turbine apparatus downstream of a combustion section of the gas turbine.

12. A device according to claim 7, wherein the acoustic liner is arranged in a gas turbine apparatus in the form of an industrial gas turbine.

13. A device according to claim 1, wherein said means comprise members adapted to conduct a film of gas along and past the acoustic liner for adjusting the acoustic impedance of the liner.

14. A device according to claim 1, wherein said members are adapted to conduct a film of gas along and past the acoustic liner for cooling thereof.

15. A device according to claim 14, wherein the gas forming the film is air.

16. A device according to claim 1, wherein said means include members adapted to heat the gas at the acoustic liner for changing the acoustic impedance of the acoustic liner.

17. A device according to claim 1, wherein said acoustic liner has a honeycomb-type cavity structure with a cover layer arranged thereon and being at least partially gas permeable, and wherein said means comprise members adapted to change the resistance to a flow of gas through the cover layer to and from the cavities.

18. A device according to claim 17, wherein said members for changing the flow resistance are adapted to enable a change of the size of through-holes arranged in said cover layer.

19. A device at an acoustic liner for an apparatus generating sound, comprising:
   members adapted to accomplish cooling of the acoustic liner through a film cooling technique, which includes conducting a film of gas along and past the acoustic liner for cooling of the liner,
   wherein the apparatus is a gas turbine,
   wherein the acoustic liner is arranged at the outlet of the gas turbine,
   wherein the acoustic liner is at least partially made of a composite material, and
   wherein the members are adapted to cool the liner to a temperature sufficiently low to avoid damaging the composite material.

20. A device at an acoustic liner for an apparatus generating sound, comprising:
- means adapted to enable changes of the value of the acoustic impedance of the liner,
- wherein said means comprise members adapted to heat the gas at the acoustic liner for changing the acoustic impedance of the acoustic liner.

21. A device at an acoustic liner for an apparatus generating sound, comprising:
- means adapted to enable changes of the value of the acoustic impedance of the liner,
- wherein said acoustic liner has a honeycomb-type cavity structure with a cover layer arranged thereon and being at least partially gas permeable,
- wherein said means comprise members adapted to change the resistance to a flow of gas through the cover layer to and from the cavities, and
- wherein said members for changing the flow resistance are adapted to enable a change of the size of through-holes arranged in said cover layer.

22. A device at an acoustic liner for an apparatus generating sound, comprising:
- means adapted to enable changes of the value of the acoustic impedance of the liner,
- wherein said means are adapted to effect an adjustment of the value of the acoustic impedance of the liner in accordance with the operation conditions of the apparatus, and
- wherein said apparatus is an aeroplane engine, and said means are adapted to cooperate with members for measuring the altitude of the aeroplane for adjusting the acoustic impedance of the liner in accordance with the current altitude.

23. A device at an acoustic liner for an apparatus generating sound, comprising:
- means adapted to enable changes of the value of the acoustic impedance of the liner,
- wherein said means are adapted to effect an adjustment of the value of the acoustic impedance of the liner in accordance with the operation conditions of the apparatus, and
- wherein said means are adapted to cooperate with members for measuring the number of revolutions of the aeroplane engine for adjusting the acoustic impedance of the liner in accordance with the current number of revolutions.

* * * * *